Figure 1:
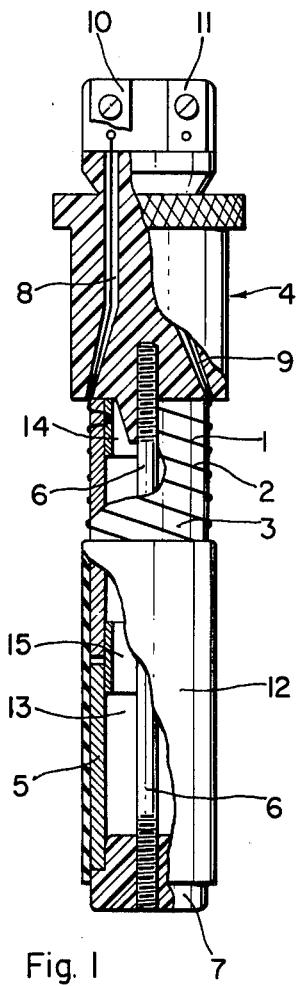

United States Patent [19]

Bamford et al.

[11] 4,172,015

[45] Oct. 23, 1979

[54] ELECTROCHEMICAL DEVICE AND ANALYTICAL METHOD

[75] Inventors: Robert A. Bamford; Charles H. Dickinson, both of Runcorn, England

[73] Assignee: Imperial Chemical Industries Limited, London, England

[21] Appl. No.: 880,877

[22] Filed: Feb. 23, 1978

[30] Foreign Application Priority Data

Feb. 28, 1977 [GB] United Kingdom ................. 8271/77

[51] Int. Cl.² ............................................. G01N 27/46
[52] U.S. Cl. ................................. 204/1 T; 204/195 R
[58] Field of Search ................... 204/195 R, 1 Y, 1 B, 204/1 N, 1 T; 324/29

[56] References Cited

U.S. PATENT DOCUMENTS

| | | | |
|---|---|---|---|
| 2,943,028 | 6/1960 | Thayer et al. | 204/195 R X |
| 3,038,848 | 6/1962 | Brewer et al. | 204/195 R |
| 3,096,258 | 7/1963 | Poulos | 204/1 T |
| 3,337,441 | 8/1967 | Goldsmith | 204/195 W |
| 3,793,158 | 2/1974 | Hamilton | 204/1 T |
| 3,856,649 | 12/1974 | Genshaw et al. | 204/195 F |

*Primary Examiner*—G. L. Kaplan
*Attorney, Agent, or Firm*—Cushman, Darby & Cushman

[57] ABSTRACT

An electrochemical device of the static-reagent type for the detection and/or monitoring of a component of a fluid, which comprises two or more electrodes in contact with a reagent which reacts chemically with the fluid component to be detected and/or monitored so as to cause an electric current to flow between the electrodes and which comprises an aqueous solution of a deliquescent substance.

11 Claims, 2 Drawing Figures

ELECTROCHEMICAL DEVICE AND ANALYTICAL METHOD

This invention relates to an electrochemical device for the analysis of fluids and in particular to an electrochemical device for detecting and/or monitoring a component of a fluid. A specific embodiment of the invention resides in an electrochemical device for the detection and monitoring of chlorine in gas streams.

It is a frequent requirement in industry to detect quickly and monitor accurately the presence and concentration of a component of fluids, especially gases. For example there is a need for rapid detection and accurate monitoring of toxic substances such as chlorine, bromine, oxides of nitrogen, chlorine dioxide and ozone gas in breathable atmospheres or in process gas streams. Numerous devices have been proposed for this purpose, including electrochemical devices wherein the substance to be detected or monitored is caused to react chemically with a reagent in contact with electrodes across which is applied a low voltage potential. An electric current is generated between the electrodes as a result of the change in composition of the reagent caused by the chemical reaction. It is with this type of electrochemical device that the present invention is concerned.

Devices of the type described above may be of the static-reagent or flowing-reagent types; in the former the reagent is static relative to the electrodes and in the latter it flows over the electrodes. Both types are capable of providing a rapid and accurate response to the fluid component to be detected and monitored, but each has its disadvantages. In static-reagent devices the reagent is usually a solution, often an aqueous solution, and prolonged exposure of the devices to gas streams results in evaporation of solvent and drying-out of the device; such devices therefore require frequent maintenance to ensure reliable operation. Flowing-reagent devices are less susceptible to drying out as fresh reagent is supplied continuously to the electrodes but they are more expensive, requiring a continuous supply of reagent, metering of the reagent flow-rate and frequent maintenance to ensure the reagent supply is operating satisfactorily.

Static-reagent devices are cheaper to install and operate than flowing-reagent devices and there is a need for a static-reagent device of simple construction which does not suffer the problem of drying out and which can operate for prolonged periods without frequent maintenance. The present invention provides such a device and resides in the use as reagent of an aqueous solution of a deliquescent substance.

According to the invention there is provided an electrochemical device of the static-reagent type for the detection and/or monitoring of a component of a fluid, which comprises two or more electrodes in contact with a reagent which reacts chemically with the fluid component to be detected and/or monitored so as to cause an electric current to flow between the electrodes and which comprises an aqueous solution of a deliquescent substance.

In using the device, which conveniently may be in the form of a probe, a low voltage potential is impressed across the electrodes and a change in the composition of the reagent resulting from reaction thereof with the fluid component to be detected/monitored causes a measurable electric current to flow between the electrodes. The size of this electric current is directly related to the amount of the fluid component reacted with the reagent and thus is an indication of the concentration of that component in the fluid. Since the reagent comprises a deliquescent substance the tendency for the device to dry out by loss of water from the reagent is countered by absorption of water from the fluid, e.g. atmospheric air, being analysed.

The electrochemical device of the invention may be in the form of any of the designs previously adopted. For instance it may comprise a cell containing the reagent in which electrodes are wholly or partly immersed and through which the fluid to be analysed is passed over the surface of the reagent. Preferably, however, the device is in the form of a probe comprising wire electrodes wrapped externally and separately around an absorbent member, for example filter paper, saturated with the reagent. Such probes can simply be placed in the fluid to be analysed and offer the advantage that any additional water collected by the deliquescent reagent when subjected to gaseous fluids containing a high proportion of moisture can be handled without seriously affecting the response or accuracy of the probe. An external continuous supply of reagent is not required.

By suitable choice of a reagent which is chemically reactive with the fluid component to be detected/monitored, the electrochemical device can be adapted for detecting and monitoring a wide variety of fluid components. By way of example, and representing a specific embodiment of the invention, chlorine in gases can be detected and monitored using a device wherein the reagent is an aqueous solution of a deliquescent halide salt, for example calcium bromide.

Since a particularly useful reaction is one which results in liberation of a halogen, especially bromine or iodine we prefer to employ deliquescent halide salts as the reagent. Examples of suitable reagents are the deliquescent bromides and iodides of calcium, lithium and magnesium.

Oxidising gases can be detected/monitored using the device of the invention, for example chlorine, bromine, chlorine dioxide, ozone, and oxides of nitrogen, e.g. nitrogen dioxide. We have found for example that calcium bromide is the preferred reagent for detecting/monitoring chlorine and that lithium-iodide is preferred for detecting/monitoring oxides of nitrogen.

The electrodes can be made of any conductive material which is chemically inert under the reaction conditions, i.e. is inert to the reagent, the gas being detected/monitored and any species formed by the reaction. Platinum is the preferred material for the electrodes, although other materials, for example platinum/rhodium alloys, may be used, if desired.

Figure 2:
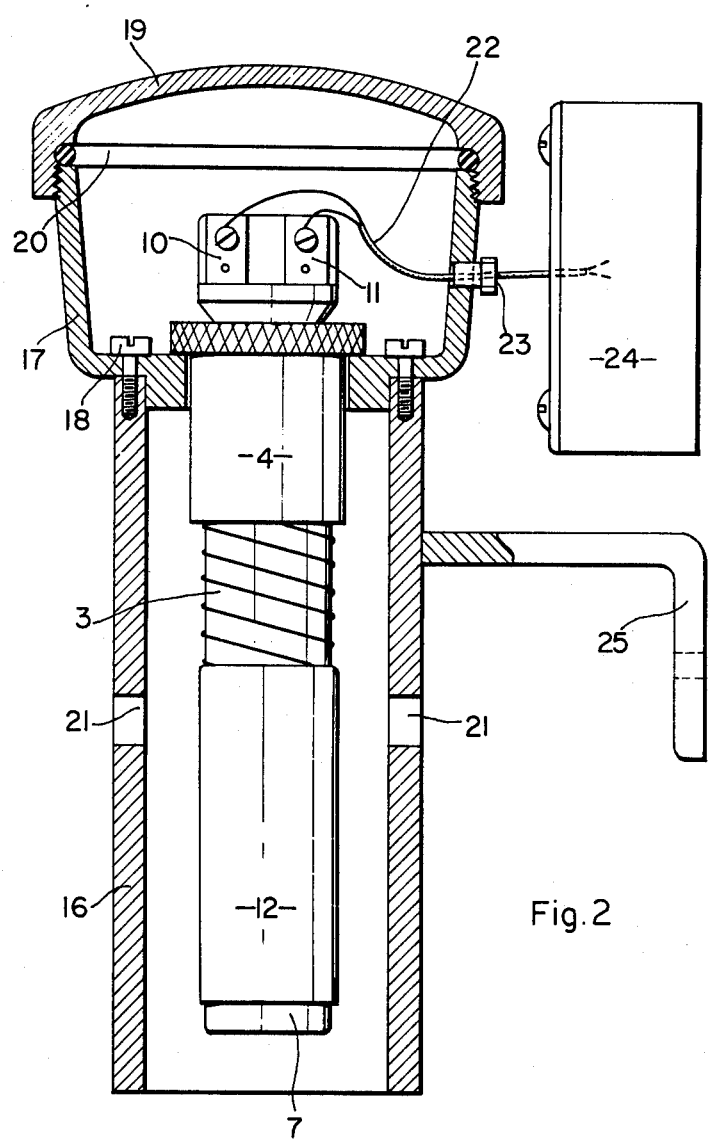

A specific embodiment of the invention will now be described by way of example only with reference to the accompanying drawings in which:

FIG. 1 shows a part-sectional side elevation of a probe useful for the detection and monitoring of chlorine in gas streams, and FIG. 2 shows the probe mounted in a weatherproof guard for use out of doors.

Referring to the drawings, the probe comprises platinum wire electrodes 1 and 2 wrapped separately and tightly around an absorbent fibrous tube 3 saturated with an aqueous solution of calcium bromide. The tube is clamped between a cylindrical polyvinyl chloride probe head 4 and an adsorbent tube 5 by means of a stainless steel clamping stud 6 and polyvinyl chloride clamping nut 7. The free ends of the wire electrodes 1 and 2 pass through holes 8 and 9 in the probe head 4 to terminals 10 and 11 mounted on the probe head 4 for connecting the electrode to a voltage supply through an appropriate electric circuit (not shown) containing a measuring device, for example an ammeter. A close-fitting sleeve 12 such as a rubber tube surrounds the adsorbent tube 5 and the end of absorbent tube 3 as shown to provide a reservoir 13 in the base of the probe to collect excess reagent over that absorbed by tubes 3 and 5. Collar inserts 14 and 15 in the probe provide fixing points for the wire electrodes 1 and 2 and reinforce the ends of tubes 3 and 5 as well as supporting the butt joint between tubes 3 and 5.

In using the probe, adsorbent tubes 3 and 5 are saturated with an aqueous solution of, say, calcium bromide and a low voltage, e.g. 0.6 volts is applied across the electrode terminals 10 and 11. The probe is inserted in the gas stream to be analysed and any chlorine in the gas reacts with the calcium bromide thereby causing an electric current to pass between the electrodes 1 and 2 through an appropriate electric circuit, the current being directly related to the concentration of chlorine in the gas stream.

In FIG. 2 the probe is shown provided with a weather guard 16 for mounting outdoors. The guard 16 is attached to a guard head 17 by means of screws 18 and a cover 19 and gasket 20 seal the guard head 17 against the ingress of water from the atmosphere. Weather guard 16 is provided with apertures 21 to assist circulation of air inside guard 16 around the probe. Terminals 10 and 11 on the probe head are connected by a signal cable 22 through a gland nut 23 to a junction box 24 for connection with a measuring circuit (not shown). A bracket 25 is provided for mounting the guarded probe on a suitable wall or vessel at any desired location.

In using the probe to detect/monitor a component of a gas stream, for example air, the probe is simply placed in the gas stream and a low voltage is applied across the electrodes 1 and 2. If the moisture content of the gas stream is low or reduces during use of the probe, then moisture will evaporate from the exposed surface of the absorbent tube 3. To replace this loss of moisture, reagent is transferred by capillary action from absorbent tube 5 immersed in reservoir 13 to absorbent tube 3. Conversely, if the moisture content of the gas stream is high or increases during use of the probe, then moisture is absorbed by the deliquescent reagent on the exposed surface of tube 3 and any resulting excess moisture drains into tube 5 and reservoir 13.

It will readily be appreciated that by a suitable choice of reagent and electrodes, the probe shown in the drawing can be rendered useful for detecting and monitoring a variety of other gaseous fluid components of gases, for example chlorine dioxide, ozone and oxides of nitrogen. Further it will be readily apparent that the signal current output provided by the probe can be used for a number of purposes, for example it can be caused to actuate visible and/or audible alarms when a particular concentration of the component being monitored is reached or exceeded, and/or it can actuate a recording system, for example a pen recorder, to provide a visible record of changes in concentration of the component over a period of time.

We claim:

1. An electrochemical device of the static-reagent type for the detection and/or monitoring of a component of a gaseous fluid, which is in the form of a probe comprising two or more wire electrodes wrapped externally and separately around an absorbent support saturated with an electrolyte which is an aqueous solution of a deliquescent substance which substance is capable of undergoing a chemical reaction with the component to be detected and/or monitored when exposed to that substance so as to cause an electric current to flow between the electrodes or to cause a change in an electric current flowing between the electrodes.

2. An electrochemical device as claimed in claim 1 wherein the absorbent member around which the electrodes are wrapped comprises a fibrous tube.

3. An electrochemical device as claimed in claim 1 or claim 2 wherein there is provided a reservoir of the reagent in communication with the absorbent member around which the electrodes are wrapped.

4. An electrochemical device as claimed in claim 3 wherein the reservoir comprises a second absorbent member in contact with the absorbent member around which the electrodes are wrapped.

5. An electrochemical device as claimed in claim 4 wherein the second absorbent member is a fibrous tube.

6. An electrochemical device as claimed in claim 4 wherein a water-impermeable sleeve surrounds the second absorbent member.

7. An electrochemical device as claimed in claim 1 wherein the electrodes are made of platinum.

8. An electrochemical device as claimed in claim 1 wherein terminals are provided for connecting the device to alarm or recorder systems.

9. An electrochemical device as claimed in claim 1 wherein the reagent is an aqueous solution of calcium bromide.

10. An electrochemical device as claimed in claim 1 wherein the reagent is an aqueous solution of lithium iodide.

11. A method for the detection and/or monitoring of a component of a fluid which comprises applying a voltage potential across the electrodes of a device as claimed in claim 1 to cause an electric current to flow between the electrodes, exposing the device to the fluid containing the component to be detected and/or monitored so causing said component to undergo a chemical reaction with the electrolyte in the device, and measuring the change resulting from the reaction in the electric current flowing between the electrodes.

* * * * *